United States Patent [19]

Hoehn

[11] 4,260,616
[45] Apr. 7, 1981

[54] ANTIMICROBIAL IMIDAZOLYLETHOXYMETHYL DERIVATIVES OF 1,3-DIOXOLO QUINOLINES

[75] Inventor: Hans Hoehn, Tegernheim, Fed. Rep. of Germany

[73] Assignee: E. R. Squibb & Sons, Inc., Princeton, N.J.

[21] Appl. No.: 121,345

[22] Filed: Feb. 14, 1980

Related U.S. Application Data

[62] Division of Ser. No. 78,344, Sep. 24, 1979.

[51] Int. Cl.³ .................. A61K 31/47; C07D 491/056
[52] U.S. Cl. ........................................ 424/258; 546/90
[58] Field of Search .......................... 546/90; 424/258

[56] References Cited

U.S. PATENT DOCUMENTS

| | | | |
|---|---|---|---|
| 3,991,201 | 11/1976 | Heeres et al. | 424/273 R |
| 4,059,705 | 11/1977 | Walker | 424/273 R |
| 4,159,380 | 6/1979 | Hoehn | 546/119 |

OTHER PUBLICATIONS

Heeres, J., et al., *J. Med. Chem.*, 19(9), 1148–1155, (1976).
Heeres, J., et al., *J. Med. Chem.*, 20(11), 1511–1519, (1977).
Walker, K., et al., *J. Med. Chem.*, 21(8), 840–843, (1978).
Walker, K., et al., *J. Med. Chem.*, 21(12), 1335–1338, (1978).
Mitscher, L., et al. *J. Med. Chem.*, 21(5), 485–489, (1978).

*Primary Examiner*—Alan L. Rotman
*Assistant Examiner*—Richard A. Schwartz
*Attorney, Agent, or Firm*—Lawrence S. Levinson; Burton Rodney

[57] ABSTRACT

Imidazolylethoxymethyl derivatives of dioxoloquinolines having the general formula

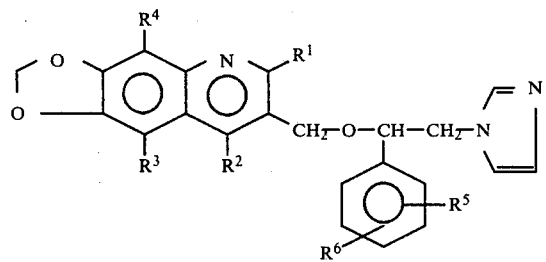

and their acid addition salts are useful as antifungal and antibacterial agents.

7 Claims, No Drawings

ANTIMICROBIAL IMIDAZOLYLETHOXYMETHYL DERIVATIVES OF 1,3-DIOXOLO QUINOLINES

This is a division of application Ser. No. 078,344, filed Sept. 24, 1979.

SUMMARY OF THE INVENTION

This invention relates to new 2-(1H-imidazol-1-yl)ethoxymethyl derivatives of 1,3-dioxolo quinolines and the acid addition salts of these compounds. These new compounds have the general formula

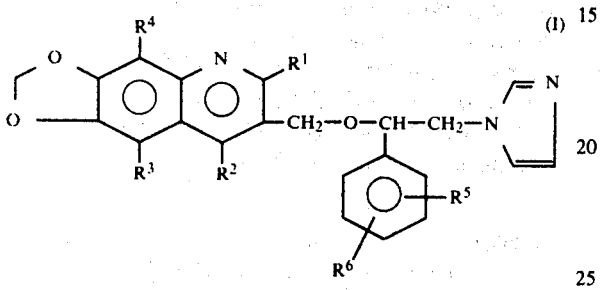

The symbols have the following meaning in formula I and throughout the specification:

$R^1$ to $R^6$ each is hydrogen, lower alkyl, hydroxy, lower alkoxy, lower alkylthio or halogen.

DETAILED DESCRIPTION OF THE INVENTION

The lower alkyl groups include straight or branched chain hydrocarbon groups containing 1 to 7 carbon atoms. Examples include methyl, ethyl, propyl, isopropyl, etc. The lower alkoxy and lower alkylthio groups include such lower alkyl groups bonded to an oxygen or sulfur, respectively, e.g., methoxy, ethoxy, propoxy, butoxy, t-butoxy, methylthio, ethylthio, propylthio, butylthio, isobutylthio, etc. In all of these the $C_1$-$C_4$, especially $C_1$-$C_2$, lower alkyl groups are preferred.

The halogens are the four common halogens, chlorine and bromine being preferred in that order. Preferably, but not necessarily, all halogens in a single compound are the same.

Preferred embodiments of this invention are compounds of formula I wherein $R^1$ to $R^6$ is hydrogen, lower alkyl of 1 to 4 carbons or halogen.

The most preferred embodiments are compounds of formula I wherein $R^1$, $R^3$ and $R^4$ each is hydrogen or halogen, especially hydrogen; $R^2$ is hydrogen or halogen, particularly chlorine, and $R^5$ and $R^6$ are attached in the 2- and 4-positions of the phenyl ring, respectively, and are preferably halogen, particularly chlorine.

The new compounds of formula I are formed by the following series of reactions.

A dioxolo quinoline-3-carboxylic acid ester of the formula

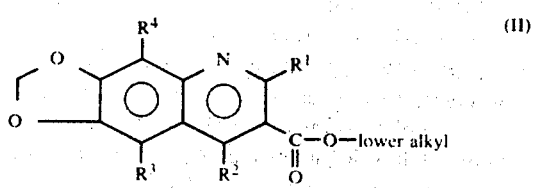

is reduced by means of a reducing agent, e.g., a metal hydride, such as lithium aluminum hydride or sodium borohydride and the like to give the alcohol of the formula

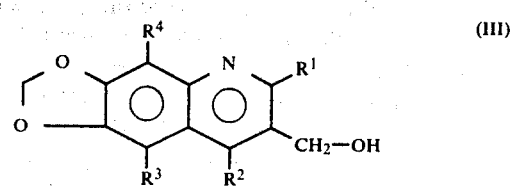

The alcohol of formula III is converted to the halomethyl derivative of the formula

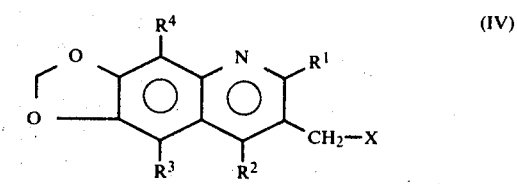

wherein X represents a halogen, preferably chlorine, bromine or iodine, by means of an inorganic acid halide, such as thionyl chloride, phosphorus oxybromide, phosphorus oxychloride, etc.

The product of formula I is then prepared by reaction of the halo compound of formula IV with a substituted 1-(phenyl)-2-(1H-imidazol-1-yl)-ethanol of the formula

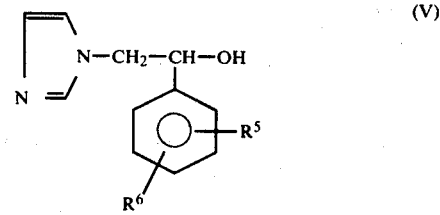

in the presence of a strong base, such as sodium hydroxide.

The inorganic acid formed during the reaction is neutralized by a base, e.g., alkali metal hydroxide, carbonate, amine, alcoholate or other similar bases known in the art.

The compounds of formula II, which are used as starting materials, are produced by the procedures described in *Journal of Medicinal Chemistry*, Vol. 11, 162, (1968). The compounds of formula V, which are used as starting materials, are produced by the general methods described in *Journal of Medicinal Chemistry*, Vol. 12, 784 (1969).

The compounds of formula I form salts which are also part of this invention. The salts include acid-addition salts, particularly the non-toxic, physiologically acceptable members. The bases of formula I form salts by reaction with one or more equivalents of any of a variety of the common inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluenesulfonate. The acid addition salts frequently provide a convenient means for isolating or purifying the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts may then be formed from the free base by reaction with one or more equivalents of acid containing the desired acid group.

The new compounds of formula I and their salts are useful as anti-fungal and anti-bacterial agents and may be used to combat infections in various mammalian species, such as mice, rats, dogs, guinea pigs and the like, particularly those due to organisms such as *Candida albicans*, as well as organisms such as *Trichomonas vaginalis* or *Trichophyton mentagrophytes*. For example, a compound or mixture of compounds of formula I or physiologically acceptable acid addition salt thereof can be administered orally to an infected animal, e.g., to a mouse, in an amount of about 5 to 25 mg per kg per day in 2 to 4 divided doses. These may be conventionally formulated in a tablet, capsule or elixir containing about 10 to 250 mg per dosage unit, by compounding the active substance or substances with the conventional excipient, vehicle, binder, preservative, flavor, etc., as called for by accepted pharmaceutical practice. Preferably they are applied topically, e.g., intravaginally in a lotion or in a conventional cream base at a concentration of about 0.01 to 3 percent by weight for a period of about 3 to 7 days, two to four times daily.

The following examples are illustrative of the invention. Temperatures are on the Celsius scale.

EXAMPLE 1

5-Chloro-6-[[1-(2,4-dichlorophenyl)-2-(1H-imadazol-1-yl)ethoxy]methyl]-1,3dioxolo[4,5-g]quinoline, hydrochloride (1:2)

A. Ethyl 5-chloro-1,3-dioxolo[4,5-g]-quinoline-7-carboxylate

A mixture of 121 g of ethyl 8-hydroxy-1,3-dioxolo[4,5-g]-quinoline-7-carboxylate (0.39 mol, prepared according to the procedure of *J. Med. Chem.*, Vol. 11, 162 (1968)) and 500 ml of phosphorus oxychloride is refluxed for 7 to 8 hours. Three quarters of the excess phosphorus oxychloride is then removed, the residue is poured onto ice, alkalized with concentrated aqueous ammonia, and the solid product is filtered off, washed with water and dried at 60° C. Yield 108.2 g (99%), m.p. 103° C.

B. 5-Chloro-1,3-dioxolo[4,5-g]quinoline-7-methanol, hydrochloride 56 g of Ethyl 5-chloro-1,3-dioxolo[4,5-g]quinoline-7-carboxylate (0.2 mol) are dissolved in 400 ml of anhydrous tetrahydrofuran. Nitrogen is passed through the flask and while stirring and cooling to −5° C., 5.7 g of lithium aluminum hydride are added a bit at a time in order to keep the reaction temperature below 0° C. Stirring is continued for an additional 2.5 hours. Then 360 ml of aqueous hydrochloric acid (3 N) are added while keeping the reaction temperature below 10° C. The precipitated title compound (40.5 g) is recrystallized from aqueous hydrochloric acid (3 N). Yield 38.1 g (70%), m.p. >300° C.

C. 5-Chloro-7-chloromethyl-1,3-dioxolo-[4,5-g]quinoline, hydrochloride 19.4 g of 5-chloro-1,3-dioxolo[4,5-g]-quinoline-7-methanol hydrochloride (0.071 mol) in 120 ml of phosphorus oxychloride are refluxed for 24 hours. After cooling, the crystallized title compound is filtered off, washed with benzene and dried at 70° C. Yield 7.8 g. Working up of the mother liquor furnishes an additional crop of 10.2 g. Total yield 18 g (87%), m.p. >300° C.

Neutralization of the hydrochloride by means of aqueous sodium hydroxide (10%) gives the free base with the melting point of 128° C.

D. 5-Chloro-6-[[1-(2,4-dichlorophenyl)-2-(1H-imidazol-1-yl)ethoxy]methyl]-1,3-dioxolo[4,5-g]quinoline, hydrochloride (1:2)

In a three-necked flask, fitted with stirrer, reflux condenser and gas inlet tube, are introduced 17.0 g of sodium hydroxide (0.425 mol) and 16 ml of water. While passing nitrogen through the flask, the solution is cooled to 45° C. and then are added 4.5 g of 1-(2,4-dichlorophenyl)-2-(1H-imidazol-1-yl)ethanol (0.0174 mol) [prepared according to *J. Med. Chem.*, Vol. 12, 784 (1969)], 0.3 g of benzyltrimethylammonium chloride and 30 ml of of tetrahydrofuran. To the mixture, which is warmed to 50° C., 5.08 g of 5-chloro-7-chloromethyl-1,3-dioxolo[4,5-g]quinoline, hydrochloride (0.0174 mol) are added portionwise. The mixture is stirred vigorously for 3 hours at 60° C. using a water bath. Then the warm mixture is transferred into a separating funnel, the lower aqueous sodium hydroxide is extracted with 15 ml of tetrahydrofuran. The combined tetrahydrofuran layers are dried by means of sodium sulfate, charcoaled and removed to a volume of about 20 ml. Addition of 250 ml of ether precipitates an oily side product (1.6 g). To the solution of the free base are added dropwise ethereal hydrochloric acid. Initially the hydrochloride of 5-chloro-6-[[1-(2,4-dichlorophenyl)-2-(1H-imidazol-1-yl)ethoxy]methyl]-1,3-dioxolo-[4,5-g]quinoline precipitates in oily form which, after standing overnight, becomes crystalline (6.6 g; m.p. 237°–238° C. dec.). After trituration with a small amount of methanol, the dihydrochloride is filtered off, washed with cooled methanol and dried at 70° C. Yield 5.5 g (58%), m.p. 242°–243° C. dec.

The following additional products of formula C are obtained by the procedure of Example 1 by reacting the unsubstituted or substituted 1-phenyl-1-(1H-imidazol-1-yl)ethanol of formula A with the unsubstituted or substituted dioxoloquinoline of formula B. The substituents apply to the respective formulas.

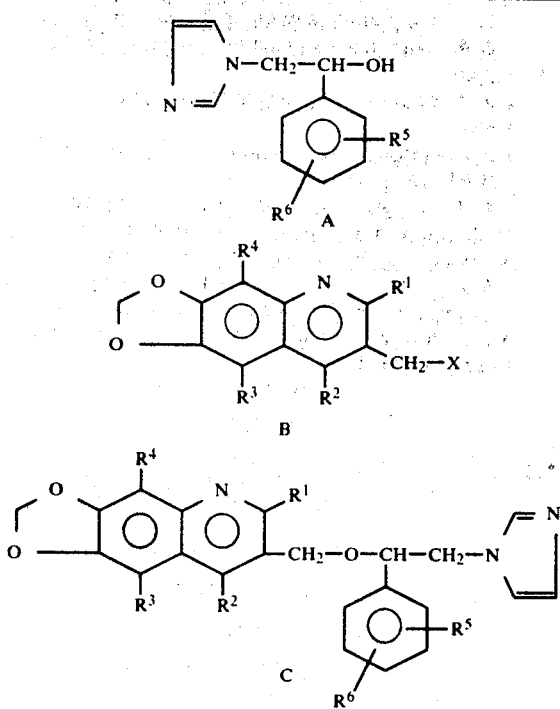

| Ex. No. | $R^1$ | $R^2$ | $R^3$ | $R^4$ | $R^5$ | $R^6$ |
|---|---|---|---|---|---|---|
| 2. | H | Cl | H | H | 2-$CH_3$ | 4-$CH_3$ |
| 3. | H | H | H | H | H | H |
| 4. | $CH_3$ | $CH_3$ | —OH | H | H | H |
| 5. | $C_2H_5$ | H | —$OC_2H_5$ | H | 2-Cl | 4-Cl |
| 6. | $C_2H_5$ | $C_2H_5$ | —$OCH_3$ | H | H | 4-Cl |
| 7. | $C_2H_5$ | $CH_3$ | Br | H | H | 3-Br |
| 8. | $C_2H_5$ | $CH_3$ | H | H | 2-Br | 4-Br |
| 9. | $C_2H_5$ | H | Br | H | 3-Br | 4-Br |
| 10. | $C_2H_5$ | H | H | H | H | 4-Cl |
| 11. | $C_2H_5$ | H | Cl | H | H | 2-Cl |
| 12. | —OH | $CH_3$ | —$OC_2H_5$ | —$CH_3$ | 2-$CH_3$ | 4-$CH_3$ |
| 13. | $C_2H_5$ | $C_3H_7$ | Cl | H | H | 4-$OCH_3$ |
| 14. | $C_2H_5$ | H | Cl | H | H | 2-$OCH_3$ |
| 15. | $C_3H_7$ | H | —OH | H | H | 3-Cl |
| 16. | H | H | Cl | —OH | 2-Cl | 4-Cl |
| 17. | $CH_3$ | $CH_3$ | H | H | H | 4-Cl |
| 18. | H | H | Cl | H | H | H |
| 19. | Cl | H | Cl | H | 2-Cl | 4-Cl |
| 20. | Cl | $CH_3$ | Cl | H | 3-Cl | 4-Cl |
| 21. | $C_2H_5$ | —OH | Cl | H | H | 4-Cl |
| 22. | $C_2H_5$ | $CH_3$ | H | Cl | 2-Cl | 4-Cl |
| 23. | H | —$SCH_3$ | Cl | H | H | 4-Cl |
| 24. | H | $CH_3$ | Cl | $CH_3$ | H | 4-Cl |
| 25. | —$OC_2H_5$ | $CH_3$ | Br | H | H | 4-Cl |
| 26. | —$SC_2H_5$ | H | Cl | H | 2-Cl | 4-Cl |
| 27. | $C_2H_5$ | H | H | H | H | 4-Br |
| 28. | H | H | —$SCH_3$ | H | 2-Cl | 4-Cl |
| 29. | —$OC_2H_5$ | $CH_3$ | Cl | H | H | 4-Cl |
| 30. | $CH_3$ | H | —$SCH_3$ | H | H | 4-$SCH_3$ |
| 31. | $C_2H_5$ | H | I | H | H | 4-Cl |
| 32. | $C_2H_5$ | H | —OH | H | 3-OH | 5-OH |
| 33. | $C_2H_5$ | $CH_3$ | —$OC_4H_9$ | H | H | 4-Cl |
| 34. | H | H | —$OC_3H_7$ | H | 2-Cl | 4-Cl |
| 35. | $C_2H_5$ | H | H | —$SCH_3$ | 2-Cl | 4-Cl |
| 36. | $C_2H_5$ | H | Cl | —OH | H | 4-Cl |

What is claimed is:
1. A compound of the formula

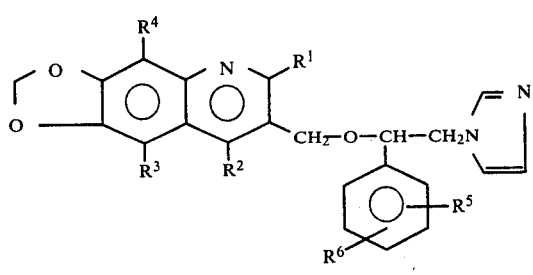

wherein $R^1$ to $R^6$ each is hydrogen, hydroxy, halogen, lower alkyl containing 1 to 7 carbons, lower alkoxy containing 1 to 7 carbons or lower alkylthio containing 1 to 7 carbons, provided that at least one of $R^1$ to $R^6$ is other than hydrogen, halogen or lower alkyl; or a physiologically acceptable acid addition salt thereof.

2. A compound as in claim 1 wherein $R^2$ is halo.

3. A compound as in claim 1 wherein $R^5$ and $R^6$ each is halo.

4. A compound as in claim 3 wherein each halo is chloro.

5. A compound as in claim 1 wherein $R^5$ is 2-chloro and $R^6$ is 4-chloro.

6. An antimicrobial composition comprising an effective amount of a compound as defined in claim 1 and a pharmaceutically acceptable carrier therefor.

7. A method for treating bacterial or fungal injections in mammals which comprises administering to a mammalian host an effective amount of a compound as defined in claim 1.

* * * * *

UNITED STATES PATENT AND TRADEMARK OFFICE
CERTIFICATE OF CORRECTION

PATENT NO. : 4,260,616

DATED : April 7, 1981

INVENTOR(S) : Hans Hoehn

It is certified that error appears in the above-identified patent and that said Letters Patent are hereby corrected as shown below:

Column 4, line 64, "phenyl-1" should read --phenyl-2--.

Signed and Sealed this

Fourth Day of August 1981

[SEAL]

Attest:

GERALD J. MOSSINGHOFF

Attesting Officer

Commissioner of Patents and Trademarks